US006660881B2

(12) United States Patent
Matsumoto et al.

(10) Patent No.: US 6,660,881 B2
(45) Date of Patent: Dec. 9, 2003

(54) PROCESS FOR PRODUCING (METH) ACRYLIC ESTER

(75) Inventors: Hajime Matsumoto, Himeji (JP); Tetsuya Kajihara, Himeji (JP); Yasuhiro Shingai, Himeji (JP); Masatoshi Ueoka, Himeji (JP); Yukihiro Yoneda, Himeji (JP); Masahiro Uemura, Himeji (JP); Sei Nakahara, Himeji (JP); Fumio Munechika, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/928,574

(22) Filed: Aug. 12, 2001

(65) Prior Publication Data
US 2002/0022739 A1 Feb. 21, 2002

(30) Foreign Application Priority Data

Aug. 18, 2000 (JP) ........................................ 2000-248862

(51) Int. Cl.[7] ........................ C07C 69/54; C07C 67/26; C07C 67/48
(52) U.S. Cl. ........................ 560/205; 560/209; 560/218
(58) Field of Search ................................ 560/218, 209, 560/205

(56) References Cited

U.S. PATENT DOCUMENTS

| 3,037,052 A | * | 5/1962  | Bortnick ................... 560/209 |
| 3,340,295 A | * | 9/1967  | Wheeler et al. ............. 560/209 |
| 3,804,884 A | * | 4/1974  | Jeffrey et al. .............. 560/209 |
| 4,365,081 A | * | 12/1982 | Shimizu et al. ............. 560/209 |
| 4,824,998 A | * | 4/1989  | Inoue et al. ................ 560/205 |
| 4,910,329 A | * | 3/1990  | McDade .................... 560/209 |
| 5,138,092 A | * | 8/1992  | Perez Pascual et al. ..... 560/205 |
| 5,866,713 A | * | 2/1999  | Suzuki et al. ............... 560/205 |

FOREIGN PATENT DOCUMENTS

GB            1003346         *   9/1965

* cited by examiner

*Primary Examiner*—Alan L. Rotman
*Assistant Examiner*—Taylor V Oh
(74) *Attorney, Agent, or Firm*—Haugen Law Firm PLLP

(57) ABSTRACT

The present invention provides a process for producing a (meth)acrylic ester which enables to obtain a (meth)acrylic ester in an excellent reaction yield. The process for producing a (meth)acrylic ester uses an alcohol and an acid as raw materials and an ion-exchange resin as a catalyst, and the process is characterized by comprising a dehydration step and an esterification step, wherein the esterification reaction step follows the dehydration step in which water impregnated in the ion-exchange resin is removed by using as a dehydrating solvent at least one member selected from the group consisting of the alcohol, the acid, and the resulting ester.

11 Claims, No Drawings

PROCESS FOR PRODUCING (METH) ACRYLIC ESTER

BACKGROUND OF THE INVENTION

A. Technical Field

The present invention relates to a process for producing a (meth)acrylic ester which uses an ion-exchange resin as a catalyst.

B. Background Art

An ion-exchange resin which has been so far used as a catalyst when a (meth)acrylic ester is produced from raw materials of an alcohol and an acid is often marketed in a moistened condition with water. When the ion-exchange resin is used in a reaction, water is usually projected into a reaction vessel in advance so as to prevent the damage of the resin. Then, the water is drained outside the reaction vessel after the ion-exchange resin is projected, so that the ion-exchange resin is packed in the reaction vessel.

However, an esterification reaction is an equilibrium reaction. Therefore, if water exists in a system of reaction, a conversion rate is low and a reaction is difficult to proceed. Therefore, the problem arises that the more water content the ion-exchange resin used as a catalyst in the esterification reaction contains, the more greatly a reaction yield falls. Accordingly, it is desired that the water content contained in the ion-exchange resin should be decreased as much as possible, before the ion-exchange resin is used in the esterification reaction.

Furthermore, a reaction to produce a hydroxyalkyl (meth)acrylate among the (meth)acrylic ester from raw materials of the alkylene oxide and the acid is not an equilibrium reaction. However, in the case where the ion-exchange resin is used as a catalyst of the esterification reaction, the more water the ion-exchange resin contains, the more greatly the concentration of raw materials in a system of reaction and a reaction yield falls. Accordingly, it is desired that the water content contained in the ion-exchange resin should be decreased as much as possible.

The decrease of water content contained in the ion-exchange resin has so far been performed by methods such as azeotropic dehydration by use of a solvent, warming under reduced pressure, and washing by use of a polar solvent.

However, if the effective utilization of a distillate as formed on the occasion of azeotropic dehydration is taken into account, it is preferred that such a solvent as forms a binary liquid phase with water is used, and that an oil phase separated from a water phase is recycled as a reflux. However, in the case where azeotropic distillation is performed with a stirred tank apparatus by use of an water-insoluble solvent, the ion-exchange resin tends to aggregate in the solvent, and in its turn an operational problem, such as a difficulty in stirring, tends to arise.

SUMMARY OF THE INVENTION

A. Objects of the Invention

An object of the present invention is to provide a process for producing a (meth)acrylic ester which enables to obtain a (meth)acrylic ester in an excellent reaction yield.

B. Disclosure of the Invention

The present inventors studied and studied with encouragement to themselves and great efforts to solve the above problems. As a result, the inventors have completed the present invention by finding out that in the case of the production of the (meth)acrylic ester, prior to performing an esterification reaction step, it becomes possible to improve a yield remarkably in the esterification reaction by performing a dehydration step of removing water impregnated in an ion-exchange resin by use of an alcohol and/or an acid of raw materials in an esterification reaction and/or the resulting ester in the esterification reaction.

Furthermore, the inventors have completed the present invention by finding out that in the case of the production of the (meth)acrylic ester from raw materials of the alkylene oxide and the acid, it becomes possible to prevent the aggregation of the ion-exchange resin on the occasion of dehydration by azeotropic removal of water as contained in the ion-exchange resin by using a solvent which not only forms a binary liquid phase with water but also has a constant solubility to water, and that it becomes possible to decrease effectively the water content as contained in the ion-exchange resin.

That is to say, the primary process for producing a (meth)acrylic ester according to the present invention is a process which uses an alcohol and an acid as raw materials and an ion-exchange resin as a catalyst, and the process is characterized by comprising a dehydration step and an esterification step, wherein the esterification reaction step follows the dehydration step in which water impregnated in the ion-exchange resin is removed by using as a dehydrating solvent at least one member selected from the group consisting of the alcohol, the acid, and the resulting ester.

Furthermore, the second process for producing a (meth)acrylic ester according to the present invention is a process which uses an alkylene oxide and an acid as raw materials and an ion-exchange resin as a catalyst, and the process is characterized by comprising a dehydration step and an esterification step, wherein the esterification reaction step follows the dehydration step in which water impregnated in the ion-exchange resin is azeotropically dehydrated by distilling a solvent (A) together with the ion-exchange resin, wherein the solvent (A) exhibits a solubility of not less than 0.05 g per 100 g of water at 20° C., and forms a binary liquid phase with water.

Furthermore, the third process for producing a (meth)acrylic ester according to the present invention is a process which uses an alkylene oxide and an acid as raw materials and an ion-exchange resin as a catalyst, and the process is characterized by comprising a dehydration step and an esterification step, wherein the esterification reaction step follows the dehydration step in which water impregnated in the ion-exchange resin is azeotropically dehydrated by distilling a solution of a mixture of solvents (B) and (C) together with the ion-exchange resin, wherein the solvent (B) is soluble in water in arbitrary ratio and wherein the solvent (C) exhibits a solubility of less than 0.05 g per 100 g of water at 20° C. and forms a binary liquid phase with water.

These and other objects and the advantages of the present invention will be more fully apparent for the following detailed disclosure.

DETAILED DESCRIPTION OF THE INVENTION

Modes for carrying out the present invention are hereinafter described in detail.

In a process for producing a (meth)acrylic ester of the present invention, prior to an esterification reaction step, it is important to perform a dehydration step to remove water impregnated in an ion-exchange resin used as a catalyst. In the dehydration step, it becomes possible to improve a yield in the esterification reaction following the dehydration step by decreasing the water content in the ion-exchange resin sufficiently in advance in the dehydration step.

In the present invention, the aforementioned dehydration step is a step of removing water impregnated in the ion-exchange resin by using as a dehydrating solvent at least one member selected from the group consisting of an alcohol, an acid (raw materials of the esterification reaction), and the resulting ester in the esterification reaction. In the case where the dehydrating solvent remains in the ion-exchange resin after dehydration, it becomes possible to improve a reaction yield effectively without preventing the esterification reaction by using as dehydrating solvents raw materials of the esterification reaction, or the resulting ester in the esterification reaction.

In the aforementioned dehydration step, a method of removing water impregnated in the ion-exchange resin is not especially limited except for using the aforementioned dehydrating solvent. For example, a method of washing the ion-exchange resin with the aforementioned solvent, a method of removing water by performing distillation after adding the aforementioned solvent to the ion-exchange resin or such is preferably enumerated.

In the case of the method of washing the ion-exchange resin with the aforementioned solvent, more specifically in the case of washing by use of a fixed-bed reactor, it is better that water of the ion-exchange resin is removed by allowing the water to pass spaces between the resins which is packed by projecting continuously the aforementioned dehydrating solvent into a reaction vessel after the ion-exchange resin is packed in the reaction vessel. It is preferred that the aforementioned dehydrating solvent is beforehand warmed, or that the reaction vessel is beforehand warmed by use of a heat resource such as steam. In this case, warming temperature is preferably in the approximate range from 30 to 120° C. Furthermore, in the case of washing by use of a stirred tank reactor, it is better that water content of the ion-exchange resin is removed by repeating such a similar operation as is to extract out only a liquid in a reaction vessel and to project the further dehydrating solvent again after projecting the ion-exchange resin and the aforementioned dehydrating solvent into the reaction vessel and stirring them for a constant period of time, or by projecting the aforementioned dehydrating solvent into the reaction vessel continuously with keeping a liquid volume in the reaction vessel constant. A method of washing the ion-exchange resin with the solvent is preferably a method of washing by use of the aforementioned fixed-bed reactor. In addition, it is desired that washing should be carried out so that the concentration of water content in liquid wastes after washing can be not more than 10 weight %, preferably not more than 5 weight %.

In the case of the aforementioned method of removing water by performing distillation after adding the solvent to the ion-exchange resin, more specifically, it is better that water content of the ion-exchange resin is removed by projecting the solvent and the ion-exchange resin into a reaction vessel to prepare a slurry state liquid, heating the liquid with stirring, and distilling the liquid. Especially, in the case where the used dehydrating solvent forms an azeotropic composition with water, azeotropic dehydration is preferable.

In the case of producing a (meth)acrylic ester from an alkylene oxide and an acid as raw materials, water impregnated in an ion-exchange resin is azeotropically dehydrated by distilling a solvent (A) together with the ion-exchange resin. In this case, the aforementioned solvent (A) is such a solvent as not only has the solubility of not less than 0.05 g per 100 g of water at 20° C., but also forms a binary liquid phase with water. The formation of a binary liquid phase between the solvent (A) and water enables to remove water content from the ion-exchange resin by azeotropic dehydration. Besides the solvent (A) having the solubility of not less than 0.05 g per 100 g of water at 20° C. enables to prevent the aggregation of the ion-exchange resin on the occasion of dehydration.

The aforementioned solvent (A) is not especially limited, as long as the solvent has not only the solubility of not less than 0.05 g per 100 g of water at 20° C., but also the solubility to such a degree as does not prevent the solvent from forming a binary liquid phase with water. Examples thereof include butanol, pentanol, hexanol, heptanol, octanol, methyl (meth)acrylate, ethyl (meth)acrylate, butyl (meth)acrylate, 2-ethylhexyl acrylate, nitrobenzene, cyclohexanol, methyl isobutyl ketone, isobutyl acetate, and the like. They may be used alone or in combination of two or more.

In the case of producing a (meth)acrylic ester from an alkylene oxide and an acid as raw materials, it is better that water impregnated in an ion-exchange resin is azeotropically dehydrated by distilling a solution of a mixture of solvents (B) and (C) together with the ion-exchange resin. The aforementioned solvent (B) is a solvent which is soluble in water in arbitrary ratio, and the aforementioned solvent (C) is a solvent which not only has the solubility of less than 0.05 g per 100 g of water at 20° C., but also forms a binary liquid phase with water. The solvent (C) in the mixture solution having the solubility of only less than 0.05 g per 100 g of water at 20° C. and the formation of a binary liquid phase with water enables to remove water content from the ion-exchange resin by azeotropic dehydration. Besides the solvent (B) in the mixture solution having the solubility to such a degree as is soluble in water enables to prevent the aggregation of the ion-exchange resin on the occasion of dehydration.

The aforementioned solvent (B) is not especially limited, as long as the solvent is soluble in water in arbitrary ratio. Examples thereof include methanol, ethanol, 1-propanol, 2-propanol, formic acid, acetic acid, propanoic acid, butanoic acid, (meth)acrylic acid, hydroxyethyl acrylate, hydroxypropyl acrylate, hydroxyethyl methacrylate, hydroxypropyl methacrylate, acetonitrile, acetone, monoethanol amine, diethanol amine, triethanol amine, glycerin, monoethylene glycol, diethylene glycol, triethylene glycol, and the like. They may be used alone or in combination of two or more. For example, in the case of using the ion-exchange resin after dehydration in the production of a hydroxyalkyl (meth)acrylate, using (meth)acrylic acid as the solvent (B) is preferable, because the (meth)acrylic acid is a raw material of the hydroxyalkyl (meth)acrylate and the ion-exchange resin is available for a reaction as it is, although the (meth)acrylic acid is attached to the ion-exchange resin after dehydration treatment.

The aforementioned solvent (C) is not especially limited, as long as the solvent is such a solvent as has not only the solubility of only less than 0.05 g per 100 g of water, but also the solubility to such a degree as does not prevent the formation of a binary liquid phase with water. Examples thereof include toluene, benzene, o-xylene, m-xylene, p-xylene, heptane, hexane, octane, cyclohexane, and the like. They may be used alone or in combination of two or more.

A mixing ratio between the aforementioned solvents (B) and (C) is preferably (B)/(C)=0.1–50 (volume ratio). When the mixing ratio is above this ratio, a condensate of vapor arising from azeotropic dehydration does not form a binary liquid phase with water, and the amount of the solvent (B) in wasted water becomes large to increase loss of the solvent (B). On the other hand, when the mixing ratio is below this ratio, the ion-exchange resin is easy to aggregate, so that the mixing ratio either above or below this ratio is disadvantageous.

Heating temperature, heating time and such are appropriately established according to a boiling point of the used solvent or such, and they are not especially limited. Heating temperature is preferably in the approximate range from 30 to 120° C., and heating time is preferably in the approximate range from 2 to 24 hours. A method of dehydrating the ion-exchange resin by distilling may be performed with any apparatus, as long as the method is a stirred tank reaction form. Especially, it is preferred that the method is performed with a stirred tank reactor combined with a distillation column. Furthermore, it is desired that distillation should be carried out until the amount of water content calculated on the amount of water content contained in the ion-exchange resin before dehydration and the amount of the packed ion-exchange resin is distilled out as a water phase, or that distillation should be carried out until the temperature reaches to such a temperature as makes the concentration of water content in a reaction vessel an aimed concentration (usually not more than 5 weight %), because the correlation between the concentration of water content and the temperature in the reaction vessel is found out if the condition of pressure is determined according to the used dehydrating solvent.

In the present invention, the aforementioned dehydration step is preferably carried out under reduced pressure. Especially, in the case where the aforementioned dehydration step is carried out by a method of removing water by performing distillation after adding the dehydrating solvent to the ion-exchange resin, distilling under reduced pressure is effective, because distilling under reduced pressure promotes dehydration. Above all, in the case where the aforementioned terminal temperature of distillation exceeds 120° C. on the occasion of dehydration by distilling, the dehydration step is more preferably performed under reduced pressure. The reduced pressure in reducing pressure is not especially limited, but it is preferably in the range from 30 to 700 hPa, more preferably from 50 to 300 hPa.

In the present invention, it is preferred that the dehydrating solvent is recovered from liquid wastes that are generated in the aforementioned dehydration step and contain water and the dehydrating solvent, and that the solvent is recycled in the dehydration step and/or the esterification reaction step. Specifically, in the case of the method of washing the ion-exchange resin with the aforementioned solvent, it is better that the aforementioned dehydrating solvent contained in liquid wastes is separated from water by distilling the liquid wastes after washing. In the case of the method of performing distillation after adding the aforementioned dehydrating solvent to the ion-exchange resin, it is better that after a generating vapor is condensed with a condenser, the resulting condensate is separated into a liquid of a water phase and an oil phase, and that the oil phase is returned into a reaction vessel as the dehydrating solvent. Furthermore, as to the dehydrating solvent dissolving in the water phase, it is better that the solvent is further separated and recovered by an operation such as distillation, and that the solvent is recycled in the dehydration step and/or the esterification reaction step. Incidentally, it is preferred that an operation of distilling liquid wastes for reuse, an operation of condensing and separating liquid wastes or such is performed with the aforementioned dehydration step at the same time, and that the solvent is recycled at any time.

In the aforementioned dehydration step, it is better that the solvent is used so that a use ratio between the ion-exchange resin and the aforementioned dehydrating solvent, a ratio of the dehydrating solvent to the volume of the ion-exchange resin in a moistened condition with water can be 1 to 30 times amount (volume), more preferably 5 to 20 times amount (volume). If the dehydrating solvent is above 30 times amount (volume), dehydration time lengthens and it is disadvantageous economically. Below 1 times amount (volume), the efficiency of dehydration falls and as a result, the esterification reaction yield falls, so that the volume of the ion-exchange resin above 30 times amount or below 1 times amount is disadvantageous.

In the aforementioned dehydration step, it is preferred that dehydration is performed until the concentration of water content in a reaction vessel packed with the ion-exchange resin becomes not more than 5 weight %. If the concentration of water content is within the aforementioned range, it becomes possible to improve a yield sufficiently without inhibiting the esterification reaction. The measurement of the water content concentration can be carried out, for example, by a method as described in the portion hereof under the heading of "DETAILED DESCRIPTION OF THE PREFERRED EMBODIMENTS".

A process for producing a (meth)acrylic ester of the present invention is a process in which the esterification reaction step following the aforementioned dehydration step is performed. In the esterification reaction step, an alcohol or an alkylene oxide, and an acid are used as raw materials and an ion-exchange resin is used as a catalyst.

As the acid, a raw material in the aforementioned esterification reaction, acrylic acid or methacrylic acid is enumerated. They may be used alone or in combination of two.

The alcohol, a raw material in the aforementioned esterification reaction is not especially limited. For example, saturated or unsaturated fatty alcohol having 1 to 12 carbon atoms, fatty cyclic alcohol having 3 to 10 carbon atoms, aromatic alcohol having 6 to 10 carbon atoms or such is enumerated. Especially, fatty alcohol or fatty cyclic alcohol having 1 to 12 carbon atoms is preferably used. Examples thereof include methanol, ethanol, propanol, isopropanol, n-butanol, isobutanol, sec-butanol, t-butanol, 1-pentanol, 2-pentanol, 3-pentanol, cyclopentanol, 1-hexanol, 2-hexanol, 3-hexanol, cyclohexanol, 1-heptanol, 2-heptanol, 3-heptanol, 1-octanol, isooctanol, 2-ethylhexanol, isononyl alcohol, lauryl alcohol, and the like. They may be used alone or in combination of two or more.

The alkylene oxide, a raw material in the aforementioned esterification reaction, is not especially limited. Examples thereof include ethylene oxide, propylene oxide, butylene oxide, styrene oxide, and the like. They may be used alone or in combination of two or more.

The ion-exchange resin to be used in the present invention is not especially limited. For example, all usually marketed ion-exchange resins such as gel type, porous type, and high-porous type are effective. These ion-exchange resins may be used alone or in combination of two or more.

In the present invention, various conditions such as a concrete method of the esterification reaction step and reaction temperature are appropriately established, and they are not especially limited. It is preferred that in the esterification reaction step, the acid, and the alcohol or the alkylene oxide, raw materials, are projected after the end of the aforementioned dehydration step to start the esterification reaction.

In the present invention, it is preferred that the aforementioned dehydration step is performed by using a reaction vessel of a reaction apparatus with which the aforementioned esterification reaction step will be performed. It becomes possible to perform the both steps continuously by carrying out in this manner the dehydration step with the reaction vessel of the apparatus used for the esterification reaction, so that it becomes possible to produce the (meth) acrylic ester with good workability.

(Effects and Advantages of the Invention)

The present invention enables to produce a (meth)acrylic ester in an excellent yield.

DETAILED DESCRIPTION OF THE PREFERRED EMBODIMENTS

Examples and comparative examples according to the present invention are hereinafter illustrated. However, the present invention is not limited thereto.

Incidentally, the concentration of water content, the water content of an ion-exchange resin, and the conversion rate of acrylic acid were measured by the following methods.

(Concentration of water content)

The concentration of water content was measured by use of Karl-Fischer moisture meter (produced by KYOTO ELECTRONICS MANUFACTURING CO., LTD.; model MKS-1s).

(Water content (the concentration of water content) of an ion-exchange resin)

The water content of an ion-exchange resin was measured by Karl-Fischer method.

(Conversion rate of acrylic acid)

The concentration (X) of acrylic acid in a raw material liquid provided for a reaction vessel in the esterification reaction step and the concentration (Y) of acrylic acid in a reaction liquid after the end of the esterification reaction were respectively measured by acid content titration, and the conversion rate of acrylic acid was calculated according to the following equation:

$$\text{The conversion rate of acrylic acid } (\%) = (X-Y)/X \times 100$$

EXAMPLE A-1

A 500 mL-reaction vessel of a fixed-bed reactor was packed with 200 mL of a cation-exchange resin (DIAION PK-208: produced by Mitsubishi Kagaku Co., Ltd.) in a moistened condition with water. A dehydration step was performed by flowing methanol as a dehydrating solvent at a flow speed of 120 mL/hr for 15 hours with heating and keeping at 65° C. the reaction vessel with an oil-bath. The water content concentration at an exit of the reaction vessel was 3.6 weight % at the time of the end of the dehydration step.

Next, the reaction vessel was continuously charged with acrylic acid at a flow speed of 70.4 mL/hr and methanol at a flow speed of 49.6 mL/hr at the same time with keeping the reaction vessel at 65° C. to start a reaction to synthesize methyl acrylate. The conversion rate of acrylic acid was 78.5% at the time when 5 hours passed after the reaction started.

Comparative Example A-1

A reaction to synthesize methyl acrylate was started in the same way as of Example A-1 except that the dehydration step of Example A-1 was not performed. As a result, the water content concentration at an exit of the reaction vessel was 13.7 weight % immediately after the reaction to synthesize methyl acrylate started, and the conversion rate of acrylic acid was 24.2% at the time when 5 hours passed after the reaction started.

EXAMPLE A-2

A 500 mL-reaction vessel of a stirred tank reactor equipped with a stirring blade, a distillation column, and a jacket for heating was packed with 155 mL of a cation-exchange resin (DIAION PK-208: produced by Mitsubishi Kagaku Co., Ltd.) in a moistened condition with water. Moreover, 200 mL of a liquid comprising 8.54 weight % of acrylic acid, 15.72 weight % of n-butanol, 73.10 weight % of n-butyl acrylate, and 2.64 weight % of water was projected into the reaction vessel. The dehydration step was carried out by drawing this slurry liquid to a vacuum of 270 hPa with stirring at the speed of 300 rpm, performing heating with the jacket for heating, and performing azeotropic distillation of three components comprising water, n-butanol, and a-butyl acrylate. After a vapor forming by azeotropic distillation was condensed with a condenser, the resulting condensate was separated into an oil phase and a water phase. The oil phase comprising n-butanol and a butyl acrylate was returned into the column as a reflux, and the water phase was disused as a drain. A liquid volume decreased, because the water phase was disused as a drain. Therefore, n-butanol was added further to keep the liquid volume constant. This dehydration operation was performed for 18 hours, and the dehydration step was terminated at the time when the temperature in the reaction vessel reached to 90° C. The water content concentration in the reaction vessel was 1.1 weight % at the time of the end of the dehydration step.

Next, after the temperature in the reaction vessel was dropped to 75° C., the reaction vessel was continuously charged with 135.4 mL/hr of acrylic acid and 252.1 mL/hr of n-butanol at the same time to start a reaction to synthesize n-butyl acrylate. The conversion rate of acrylic acid was 87.3% at the time when 3 hours passed after the reaction started.

Comparative Example A-2

A reaction vessel of a stirred tank reactor was packed with a cation-exchange resin in a moistened state with water, a liquid comprising acrylic acid, n-butanol, n-butyl acrylate, and water in the same way as of Example A-2. This slurry liquid was drawn to a vacuum of 270 hPa with stirring at the speed of 300 rpm, and heated with the jacket for heating. At the time when the temperature in the reaction vessel reached to 75° C. (the state in which azeotropy did not happen), the reaction vessel was continuously charged with 135.4 mL/hr of acrylic acid and 252.1 mL/hr of n-butanol at the same time to start a reaction to synthesize n-butyl acrylate. The water content concentration in the reaction vessel was 15.2 weight % immediately after the reaction to synthesize n-butyl acrylate started, and the conversion rate of acrylic acid was 26.7% at the time when 3 hours passed after the reaction started.

Dehydration of an Ion-exchange Resin

EXAMPLE B-1-1

A 5 L-reaction vessel equipped with a stirrer, jacket for heating, condenser, oil-water separator, and vacuum pump was charged with 2 L of a strong basic anion-exchange resin (PA316: produced by Mitsubishi Kagaku Co., Ltd.), which the water content in a moistened condition (the water content contains water retained between spaces of the resins. The water content as described below means this water content) was 80 weight % of the strong basic anion-exchange resin. Moreover, 1.5 L of acrylic acid, 0.5 L of toluene, and 10 g of hydroquinone monomethyl ether were projected into the reaction vessel. Next, this slurry liquid was drawn to a vacuum of 133 hPa with stirring, and was heated. After a forming vapor at this time was condensed with a condenser, the resulting condensate was introduced into the oil-water separator to separate into a water phase and an oil phase. The oil phase which main component was toluene was returned into the reaction vessel as a reflux, and the water phase was disused as a drain. Because the disuse of a drain brings about a decrease of a liquid volume in the reaction vessel, toluene was added to the reaction vessel continuously so that the liquid volume might be constant. A distilling operation was carried out for 12 hours in the above way. Distillation was stopped at the time when the temperature of the slurry liquid reached to 55° C. The water content concentration in the slurry liquid as measured after the stoppage of distillation was 0.3 weight %. During distillation, there occurred neither the aggregation of the ion-exchange resin nor the operational problem of distillation.

EXAMPLE B-1-2

The same reaction vessel as used in Example B-1-1 was charged with 2 L of a strong basic anion-exchange resin (PA316: produced by Mitsubishi Kagaku Co., Ltd.), which the water content in a moistened condition was 80 weight % of the strong basic anion-exchange resin. Moreover, 2 L of n-butanol was projected into the reaction vessel. Next, this slurry liquid was drawn to a vacuum of 67 hPa with stirring, and was heated. After a forming vapor at this time was condensed with a condenser, the resulting condensate was introduced into an oil-water separator to separate into a water phase and an oil phase. The oil phase which main component was n-butanol was returned into the reaction vessel as a reflux, and the water phase was disused as a drain. Because the disuse of a drain brings about a decrease of a liquid volume in the reaction vessel, n-butanol was added to the reaction vessel continuously so that the liquid volume might be constant. A distilling operation was carried out for 14 hours in the above way. Distillation was stopped at the time when the temperature of the slurry liquid reached to 57° C. The water content concentration in the slurry liquid as measured after the stoppage of distillation was 0.4 weight %. During distillation, there occurred neither the aggregation of the ion-exchange resin nor the operational problem of distillation.

EXAMPLE B-1-3

A distilling operation was carried out in the same way as of Example B-1-1 except that 0.18 L of acrylic acid and 1.8 L of toluene were projected after the injection of 2 L of a strong basic anion-exchange resin (PA316: produced by Mitsubishi Kagaku Co., Ltd.). This distilling operation was carried out for 12 hours in the above way. Distillation was stopped at the time when the temperature of a slurry liquid reached to 53° C. The water content concentration in the slurry liquid as measured after the stoppage of distillation was 0.3 weight %. During distillation, there occurred neither the aggregation of the ion-exchange resin nor the operational problem of distillation.

EXAMPLE B-1-4

A distilling operation was carried out in the same way as of Example B-1-1 except that 2 L of acrylic acid and 0.04 L of toluene were projected after the injection of 2 L of a strong basic anion-exchange resin (PA316: produced by Mitsubishi Kagaku Co., Ltd.). This distilling operation was carried out for 14 hours in the above way. Distillation was stopped at the time when the temperature of a slurry liquid reached to 55° C. The water content concentration in the slurry liquid as measured after the stoppage of distillation was 0.4 weight %. During distillation, there occurred neither the aggregation of the ion-exchange resin nor the operational problem of distillation.

Comparative Example B-1-1

The same reaction vessel as used in Example B-1-1 was charged with 2 L of a strong basic anion-exchange resin (PA316: produced by Mitsubishi Kagaku Co., Ltd.), which the water content in a moistened condition was 80 weight % of the strong basic anion-exchange resin. Moreover, 2 L of toluene alone was projected into the reaction vessel. Next, this slurry liquid tried to be stirred. However, the slurry liquid came to be separated completely into a toluene phase of low density, the upper layer, and a resin phase of high density containing much water, the lower layer. Mixing both layers by stirring was impossible. If this slurry liquid had been drawn to a vacuum and heated, it would have been in a danger not only of flashing of the liquid because the water phase of a lower boiling point than toluene was covered with the toluene phase, but also of the deterioration of the ion-exchange resin owing to a local overheating of the ion-exchange resin. Therefore, a distilling operation was stopped.

Production of a Hydroxyalkyl (Meth)acrylate

EXAMPLE B-2-1

Following Example B-1-1, production of hydroxyethyl (meth)acrylate was carried out using the ion-exchange resin as treated with dehydration in Example B-1-1. The slurry liquid was extracted through a drain valve of the reaction vessel, because toluene usually remained in the slurry liquid after the dehydration treatment in Example B-1-1. Next, the reaction vessel was continuously supplied with 550 g/hr of acrylic acid containing hydroquinone monomethyl ether in an amount of 0.5 weight % and 500 g/hr of ethylene oxide. The reaction vessel was heated to the temperature of 60° C. The pressure inside the reaction vessel was kept 3800 hPa. A reaction was carried out continuously in the residence period of 3 hours. When the composition of a reaction liquid at an exit of the reaction vessel after 10 hours was analyzed, acrylic acid was in an amount of 10.2 weight %. The below-mentioned conversion rate of acrylic acid was 80.5%.

(Conversion rate of acrylic acid)

The concentration (X) of acrylic acid provided for a reaction vessel and the concentration (Y) of acrylic acid in a reaction liquid were respectively measured by acid content titration, and calculated according to the following equation:

$$\text{Conversion rate of acrylic acid } (\%) = (X-Y)/X \times 100$$

EXAMPLE B-2-2

Following Example B-1-1, production of hydroxypropyl (meth)acrylate was carried out using the ion-exchange resin as treated with dehydration in Example B-1-1. The slurry liquid was extracted through a drain valve of the reaction vessel, because toluene usually remained in the slurry liquid after the dehydration treatment in Example B-1-1. Next, the reaction vessel was continuously supplied with 550 g/hr of acrylic acid containing hydroquinone monomethyl ether in an amount of 0.5 weight % and 650 g/hr of propylene oxide. The reaction vessel was heated to the temperature of 60° C. The pressure inside the reaction vessel was kept 2500 hPa. A reaction was carried out continuously in the residence period of 3 hours. When the composition of a reaction liquid at an exit of the reaction vessel after 10 hours was analyzed, acrylic acid was in an amount of 10.8 weight %. The aforementioned conversion rate of acrylic acid was 76.4%.

EXAMPLE B-2-3

Following Example B-1-2, hydroxypropyl reaction of n-butanol was carried out using the ion-exchange resin as treated with dehydration in Example B-1-2. N-butanol remaining in the slurry liquid after the dehydration treatment in Example B-1-2 was also used in a reaction as it was. Next, the reaction vessel was continuously supplied with 500 g/hr of n-butanol and 500 g/hr of propylene oxide. The reaction vessel was heated to the temperature of 60° C. The pressure inside the reaction vessel was kept 2500 hPa. A reaction was carried out continuously in the residence period of 5 hours. When the composition of a reaction liquid at an exit of the reaction vessel after 15 hours was analyzed, n-butanol was in an amount of 17.5 weight %. The below-mentioned conversion rate of n-butanol was 65.0%.

(Conversion rate of n-butanol)

The concentration (X) of n-butanol supplied for a reaction vessel and the concentration (Y) of n-butanol in a reaction liquid were respectively measured by gas chromatography, and calculated according to the following equation:

Conversion rate of n-butanol $(\%) = (X-Y)/X \times 100$

Comparative Example B-2-1

Production of hydroxyethyl acrylate was carried out in the same way as of Example B-2-1 except for using an ion-exchange resin (A strong basic anion-exchange resin (PA316: produced by Mitsubishi Kagaku Co., Ltd.), which the water content was 80 weight %) as untreated with dehydration. Some of water content as retained by the ion-exchange resin, which accumulated by gravity at the bottom of the reaction vessel which the ion-exchange resin was projected into, was extracted through a drain valve. When the composition of a reaction liquid at an exit of the reaction vessel 10 hours after the start of a reaction was analyzed, acrylic acid was in an amount of 35.2 weight %. The aforementioned conversion rate of acrylic acid was 22.6%.

Comparative Example B-2-2

Production of hydroxypropyl acrylate was carried out in the same way as of Example B-2-2 except for using an ion-exchange resin (A strong basic anion-exchange resin (PA316: produced by Mitsubishi Kagaku Co., Ltd.), which the water content was 80 weight %) as untreated with dehydration. Some of water content as retained by the ion-exchange resin, which accumulated by gravity at the bottom of the reaction vessel which the ion-exchange resin was projected into, was extracted through a drain valve. When the composition of a reaction liquid at an exit of the reaction vessel 10 hours after the start of a reaction was analyzed, acrylic acid was in an amount of 31.8 weight %. The aforementioned conversion rate of acrylic acid was 21.4%.

Comparative Example B-2-3

Hydroxypropyl reaction of n-butanol was carried out in the same way as of Example B-2-3 except for using an ion-exchange resin (A strong basic anion-exchange resin (PA316: produced by Mitsubishi Kagaku Co., Ltd.), which the water content was 80 weight %) as untreated with dehydration. Some of water content as retained by the ion-exchange resin, which accumulated by gravity at the bottom of the reaction vessel which the ion-exchange resin was projected into, was extracted through a drain valve. When the composition of a reaction liquid at an exit of the reaction vessel 15 hours after the start of a reaction was analyzed, n-butanol was in an amount of 37.0 weight %. The aforementioned conversion rate of n-butanol was 18.0%.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A process of or producing a (meth)acrylic ester, which uses an alcohol and an acid as raw materials and an ion-exchange resin as a catalyst, wherein said alcohol used as said raw material comprises at least one alcohol selected from the group consisting of saturated fatty alcohol having 1 to 12 carbon atoms, unsaturated fatty alcohol having at least 2 to 12 carbon atoms, fatty cyclic alcohol having 3 to 10 carbon atoms, and aromatic alcohol having 6 to 10 carbon atoms, wherein said acid used as said raw material comprises at least one acid selected from the group consisting of acrylic acid and methacrylic acid, wherein said ion-exchange resin used as a catalyst comprises at least one ion-exchange resin selected from the group consisting of gel resins, porous resins, and high-porous resins, with the process comprising (a) a dehydration step in which water impregnated in the ion-exchange resin is removed by using a dehydrating solvent and (b) an esterification reaction step, wherein the esterification reaction step follows the dehydration step, wherein said dehydrating solvent is at least one member selected from the group consisting of said alcohol used as said raw material, said acid used as said raw material, and (said (meth)acrylic ester produced by said alcohol and said acid.

2. A process according to claim 1, wherein the dehydration step is performed by using a reaction vessel of a reaction apparatus with which the esterification reaction step will be performed.

3. A process according to claim 1, wherein the dehydration step includes the step of washing the ion-exchange resin with the dehydrating solvent.

4. A process according to claim 1, wherein the dehydration step includes the step of performing distillation after adding the dehydrating solvent to the ion-exchange resin.

5. A process according to claim 4, wherein the dehydration step is performed under reduced pressure, wherein said reduced pressure is 30–700 hPa.

6. A process according to claim 1, which further comprises the steps of; recovering the dehydrating solvent from liquid wastes that are generated in the dehydration step and Contain water and the dehydrating solvent; and recycling the recovered dehydrating solvent to the dehydration step and/or the esterification reaction step.

7. A process for producing a (meth)acrylic ester, which uses an alkylene oxide and an acid as raw materials and an ion-exchange resin as a catalyst, wherein said alkylene oxide used as said raw material comprises at least one alkylene oxide selected from the group consisting of ethylene oxide, propylene oxide, butylene oxide, and styrene oxide, wherein said acid used as said raw material comprises at least one acid selected from the group consisting of acrylic acid and methacrylic acid, wherein said ion-exchange resin used as a catalyst comprises at least one ion-exchange resin selected from the group consisting of gel resins, porous resins, and high-porous resins, with the process comprising a dehydration step and an esterification reaction step, wherein the esterification reaction step follows the dehydration step, wherein the dehydration step comprises the step of azeotropically dehydrating the ion-exchange resin by distilling a solvent (A) together with the ion-exchange resin to remove water impregnated in the ion-exchange resin, wherein solvent (A) is at least one member selected from the group consisting of butanol, pentanol, hexanol, heptanol, octanol, methyl (meth)acrylate, ethyl (meth) acrylate, butyl (meth)acrylate, 2-ethylhexyl acrylate, nitrobenzene, cyclohexanol, methyl isobutyl ketone and isobutyl acetate.

8. A process f or producing a (meth)acrylic ester, which uses an alkylene oxide and an acid as raw materials and an ion-exchange resin as a catalyst, wherein said alkylene oxide used as said raw material comprises at least one alkylene oxide selected from the group consisting of ethylene oxide, propylene oxide, butylene oxide, and styrene oxide, wherein said acid used as said raw material comprises at least one acid selected from the group consisting of acrylic acid and methacrylic acid, wherein said ion-exchange (resin used as a catalyst comprises at least one ion-exchange resin selected from the group consisting of gel resins, porous resins, and high-porous resins, with the process comprising a dehydration step and an esterification reaction step, wherein the esterification reaction step follows the dehydration step, wherein the dehydration step comprises the step of azeotropically dehydrating the ion-exchange resin by distilling a solvent together with the ion-exchange resin to remove water impregnated in the ion-exchange resin, wherein said solvent is a solution of a mixture of solvents (B) and (C), wherein the solvent (B) is soluble in water in an arbitrary ratio and wherein solvent (C) is at least one member selected from the group consisting of toluene, benzene, o-xylene, m-xylene, p-xylene, heptane, hexane, octane and cyclohexane, and wherein the solvent (B) is at least one member selected from the group consisting of methanol, ethanol, 1-propanol, 2-propanol, formic acid, acetic acid, propanoic acid, butanoic acid, (meth)acrylic acid, hydroxyethyl acrylate, hydroxypropyl acrylate, hydroxyethyl, methacrylate, hydroxypropyl methacrylate, acetonitrile, acetone, monoethanol amine, diethanol amine, triethanol amine, glycerin, monoethyleneglycol, diethylene glycol and triethylene glycol.

9. A process according to claim 8, wherein the mixing ratio between the solvents (B) and (C) is (B)/(C)=0.1–50 (volume ratio).

10. A process according to claim 8, wherein (meth)acrylic acid is used as the solvent (B).

11. A process according to claim 8, wherein the (meth) acrylic ester is a hydroxyalkyl (meth)acrylate.

* * * * *